(12) United States Patent
Jeannin

(10) Patent No.: US 11,721,258 B2
(45) Date of Patent: Aug. 8, 2023

(54) VISUAL COMFORT DEVICE

(71) Applicant: BOARDING RING, Ollioules (FR)

(72) Inventor: Hubert Jeannin, Ollioules (FR)

(73) Assignee: BOARDING RING, Ollioules (FR)

( * ) Notice: Subject to any disclaimer, the term of this patent is extended or adjusted under 35 U.S.C. 154(b) by 0 days.

(21) Appl. No.: 17/419,798

(22) PCT Filed: Dec. 17, 2019

(86) PCT No.: PCT/FR2019/053131
§ 371 (c)(1),
(2) Date: Jun. 30, 2021

(87) PCT Pub. No.: WO2020/141269
PCT Pub. Date: Jul. 9, 2020

(65) Prior Publication Data
US 2022/0076603 A1    Mar. 10, 2022

Related U.S. Application Data

(60) Provisional application No. 62/788,357, filed on Jan. 4, 2019.

(51) Int. Cl.
*G09G 3/20* (2006.01)
*B60N 2/879* (2018.01)
(Continued)

(52) U.S. Cl.
CPC ............... *G09G 3/20* (2013.01); *B60N 2/879* (2018.02); *G02B 27/0172* (2013.01);
(Continued)

(58) Field of Classification Search
CPC .. G09G 3/20; G09G 2340/0464; B60N 2/879; G02B 27/0172; G02B 2027/014;
(Continued)

(56) References Cited

U.S. PATENT DOCUMENTS 9,862,312 B2    1/2018   Sivak et al.
9,994,228 B2    6/2018   Krueger
(Continued)

FOREIGN PATENT DOCUMENTS

DE    102017005982 A1    2/2018
WO         0122151 A1    3/2001

OTHER PUBLICATIONS

International Search Report (PCT/ISA/210) with English translation and Written Opinion KPCT/ISA/237) dated Mar. 26, 2020, by the European Patent Office as the International Searching Authority for International Application No. PCT/FR2019/053131. (12 pages).

*Primary Examiner* — Amit Chatly
(74) *Attorney, Agent, or Firm* — Buchanan Ingersoll & Rooney PC

(57) ABSTRACT

The invention relates to a visual comfort device comprising at least one inertial sensor, a processing unit and at least one screen. The screen is intended to be positioned laterally in a peripheral field of vision of a user. The processing unit is coupled to the inertial sensor and to the screen. The device is configured to display, on the screen, an inertial matrix representative of an inertial information item, the displayed inertial matrix comprising a maximum of sixteen points and/or line crossings.

8 Claims, 6 Drawing Sheets

(51) Int. Cl.
  *G02B 27/01* (2006.01)
  *G06F 1/16* (2006.01)
(52) U.S. Cl.
  CPC ...... *G06F 1/1694* (2013.01); *G02B 2027/014* (2013.01); *G02B 2027/0178* (2013.01); *G09G 2340/0464* (2013.01)
(58) Field of Classification Search
  CPC .......... G02B 2027/0178; G06F 1/1694; A61M 2021/0044; A61M 2205/50; A61M 2230/63; A61M 21/00
  See application file for complete search history.

(56) References Cited

U.S. PATENT DOCUMENTS

| | | | | |
|---|---|---|---|---|
| 2017/0285344 A1* | 10/2017 | Benko | ................... | G06T 19/006 |
| 2017/0291538 A1* | 10/2017 | Sivak | ...................... | B60Q 3/70 |
| 2021/0331612 A1* | 10/2021 | Sakota | ................... | B60N 2/879 |

* cited by examiner

Fig. 8
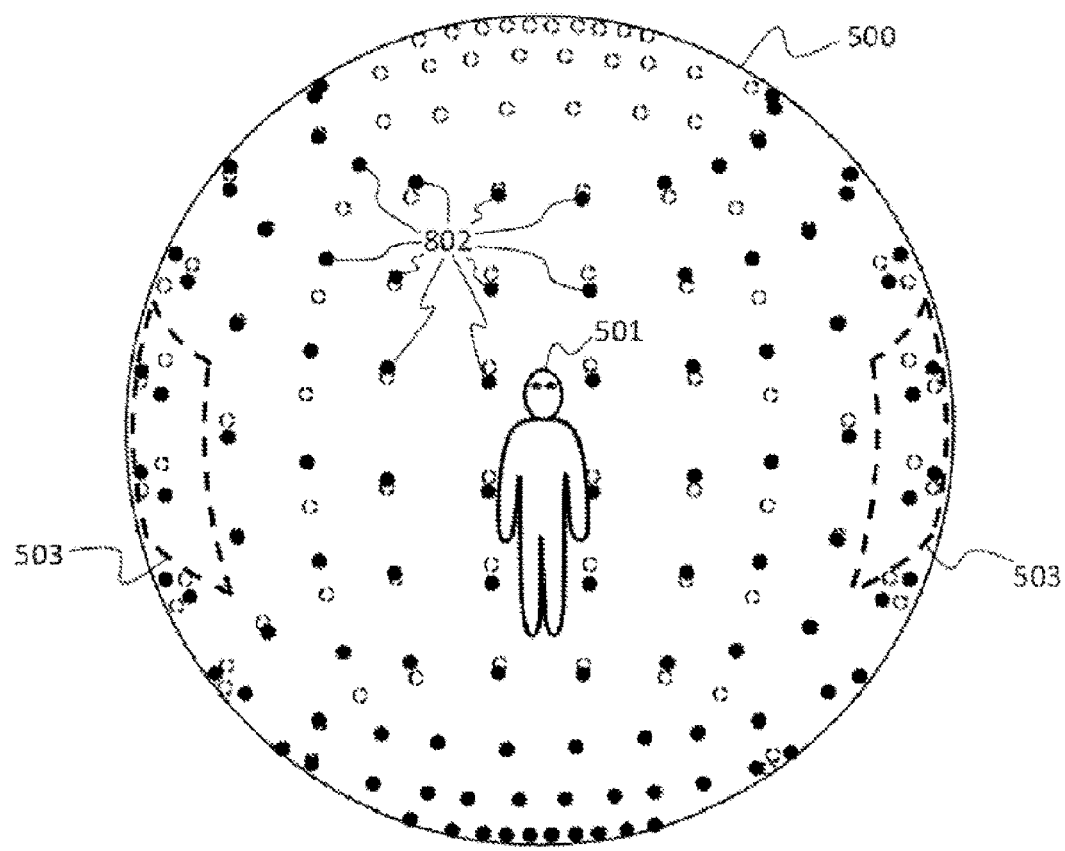
Fig. 9
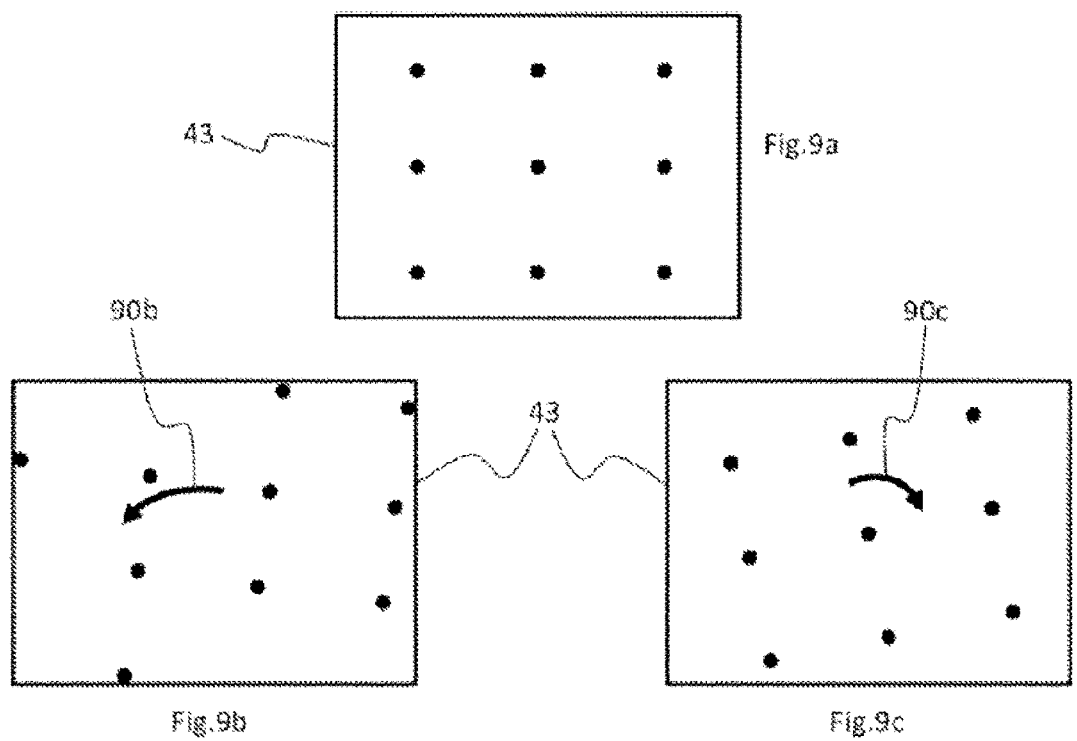
Fig.9a
Fig.9b  Fig.9c

VISUAL COMFORT DEVICE

FIELD OF THE INVENTION

The invention relates to a visual comfort device. More particularly, the invention relates to visual reference devices, advantageously lateral or bilateral, intended in particular to remedy vigilance disorders in situations of empty visual field, or on the other hand, visual confinement.

TECHNICAL BACKGROUND

As a result of the difficulty of its inertial stabilization and weak reference, the visual field can cause claustrophobia, agoraphobia, various types of vertigo, various migraines, kinetosis or cybersickness, etc. and in many cases discomfort, stress and therefore, a loss of vigilance. Such discomfort can prove to be a serious inconvenience.

Preferably, but non-limitatively, such visual comfort devices can be used in the context of applications associated with enclosed or partially enclosed spaces, which may be mobile, for example carrying passengers, including animals, such as, non-limitatively, cabins, cockpits and cages of means of transport; vehicles, trains, aircraft, boats, but also fixed or mobile spaces that may possibly allow the display of images, such as in particular cinemas, cabins of passenger lifts and other types such as ski lifts; radiology and/or scanner appliances, fixed or mobile simulators, virtual reality masks for mixed or augmented reality.

A difference of perception between vision and the balance perceived by the inner ear occurs when an individual is placed in a moving environment without visually perceiving this movement, and vice versa. In such a situation, the eye perceives a stable environment inside a moving object, for example inside a cabin of a moving ship, while the inner rear perceives the opposite information. The individual perceives the movement of the ship. This contradiction or difference of perception is the cause of motion sickness comprising non-limitatively, seasickness, airsickness, carsickness, etc. also called kinetosis. Such kinetosis can also appear during the use of simulators and/or virtual and/or augmented reality masks. In this case, the information perceived by the inner ear and the information that the individual sees are in contradiction.

In order to overcome such inconvenience, different anti-kinetosis devices have been developed. For example, international patent application WO01/22151 proposes, to counter kinetosis, glasses containing a visual balancing device that is added to, or integrated with, any support, in this case to said glasses, which must be positioned in the peripheral visual field of the individual. It is constituted by a tube or a pipe or any other recipient in a closed loop, impermeable, transparent or translucent, in which are contained at least two substances that are present in different states and/or masses, such as for example, one in a liquid form, the other in a gaseous form, such that the interfaces between said substances mark visible level reference points.

The tube in a closed loop adopts the general shape of a ring or a torus inserted or integrated in a lens or eyepiece, a frame with or without a lens, or even fixed by bonding or clipping. At least one of the two substances that the tube contains is a liquid, such that it functions in a manner fundamentally comparable to that of the inner ear.

Alternatively, the visual balancing device can exhibit the form of a virtual or light image of the same type, projected or integrated in a glasses lens, obtained by means of an electronic device constituted for example by a sensor, in the form of a gyroscope or any other source capturing information from an environmental or mobile position, arranged or adapted to detect the variations of the position with respect to gravity. Optionally after computer processing, the items of information are then made available to the eye or eyes of a user by an imaging or lighting system, for example in the form of an inner or outer perimeter of a screen, or in the form of an animation or else by one or more wall-mounted or other screens, or even in the form of a lighting system, for example by light beams, or in the form of columns or displays using light-emitting diodes.

In such devices, problems of perception may arise, for example due to variations in the lighting level. Consequently, the devices may be less effective as a result of a poor peripheral arrangement of the contrast or the lighting. Moreover, the items of information delivered by such anti-kinetosis devices prove too numerous, and thus very difficult to distinguish when analysed, to be able to obtain the expected efficacy.

When multiple items of visual information are brought into the visual field, as they are naturally in any landscape, in particular a large quantity of inertial messages, the perception strategy intuitively brought to bear is less immediate, very complex, and of difficult access. Indeed, the greater the quantity of items of information, the more cumbersome is this quantity, therefore making the discrimination thereof more difficult and thus slower, the volume of inertial information interfering, by sheer size, with its efficacy.

SUMMARY OF THE INVENTION

Through its structure and its composition, the invention makes it possible to solve all or part of the aforementioned drawbacks.

More particularly, a visual comfort device according to the invention overcomes such difficulties by proposing a new arrangement and a new organization of an item of visual information reduced to its most simple minimum, rapidly accessible and capable of analysis by the brain of a human or animal user. The visual information made available by a visual comfort device according to the invention, in the form of an ergonomic content, simplified and summarized, consequently induces comfort and vigilance going well beyond the reduction, or even the suppression, of kinetosis proposed by the current devices.

Preferably, but non-limitatively, a visual comfort device according to the invention can be used in the context of application associated with enclosed or partially enclosed spaces, possibly mobile, carrying passengers for example, including animals, such as non-limitatively cabins, cockpits and cages of means of transport; vehicles, trains, aircraft, boats, and also fixed or mobile spaces that may possibly allow the display of images, such as in particular radiology and/or scanner appliances, cinemas, cabins of passenger lifts and other types such as ski lifts, fixed or mobile simulators, virtual reality masks for mixed or augmented reality.

More particularly, the invention proposes a visual comfort device containing at least one inertial sensor, a processing unit and at least one screen. The screen is intended to be positioned laterally in a peripheral visual field of a user. The processing unit is coupled to the inertial sensor and to the screen. The device is configured to display on the screen an inertial matrix representative of an item of inertial information, said displayed inertial matrix containing a maximum of sixteen points and/or line intersections.

According to a preferred embodiment, the device can contain two screens arranged to be placed in the outer monocular field of each eye of a user, each screen displaying an inertial matrix representing the inertial information.

In order to be more efficacious, the inertial matrix displayed on a screen can contain at most nine points and/or line intersections.

According to a particular embodiment, the inertial sensor can be firmly fixed to the screen and can supply the inertial information to the processing unit, the inertial information being representative of an inertial orientation of said screen.

The inertial sensor can comprise one or more of the types of sensors selected from the following list: one or more accelerometers, gyroscope, inertial reference system, magnetic field detector.

The processing unit can be configured to produce an image containing the inertial matrix oriented and displaced on the screen as a function of the inertial information received from the sensor.

More particularly, the processing unit can be configured to:
produce a virtual matrix around the user having a position fixed in space,
position the screen with respect to the virtual matrix as a function of the inertial information, and
extract the image representative of the inertial matrix to be displayed on the screen as a function of the positioning of the screen.

In order to implement the device in a vehicle, the device can also contain a fastening means for a vehicle seat and at least one linking arm linking the at least one screen to the fastening means such that the screen is placed at the level of one side of the head of a user of the seat, so that the screen is placed in the peripheral visual field of said user.

According to an embodiment, the invention can be a pair of glasses comprising two sidearms intended to cooperate with the ears of a user, said pair of glasses containing at least one visual comfort device, at least one screen being fastened on one of the sidearms such that the screen is placed laterally in the peripheral visual field of the user.

According to another embodiment, the invention can be a virtual reality mask comprising a housing intended to be placed in the visual field of a user and containing at least one main screen placed in the central visual field of a user, said mask containing a visual comfort device in which the two screens can be placed laterally inside the housing such that they are placed in the peripheral visual field of a right eye and a left eye of a user, respectively.

BRIEF DESCRIPTION OF THE FIGURES

The invention will be better understood and other characteristics and advantages thereof will become apparent on reading the following description of particular embodiments of the invention, given by way of illustrative, non-limitative examples, with reference to the attached drawings, in which:

FIGS. 8 and 9 illustrate a second preferred embodiment of an inertial matrix according to the invention.

DETAILED DESCRIPTION

Figure 1:
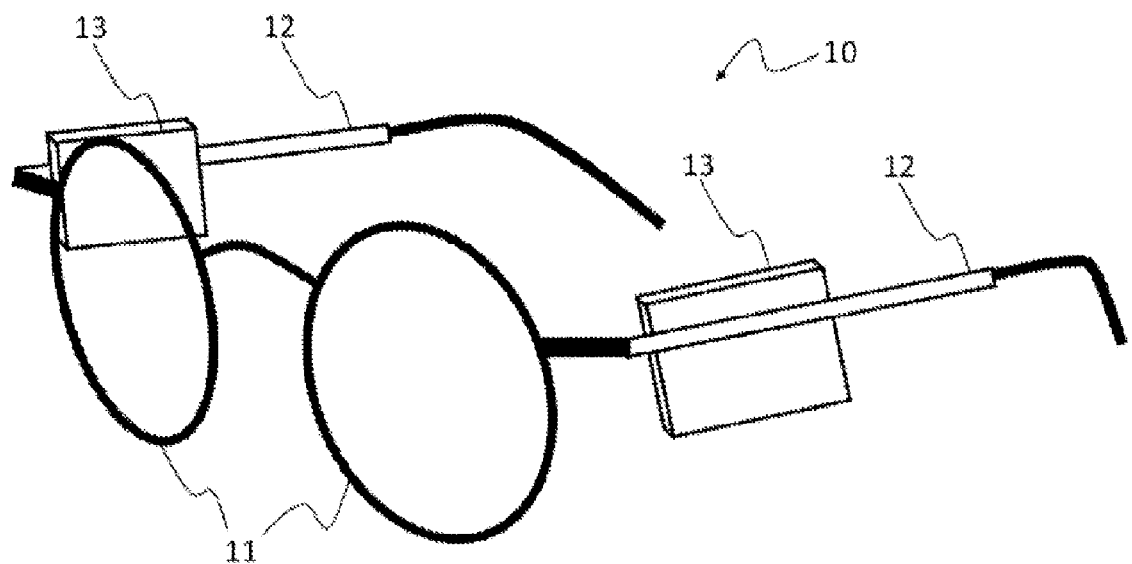
FIG. 1 represents a first embodiment of the invention in the form of glasses.

With respect to the consideration that the peripheral visual field is more particularly dedicated to this reading matrix, or inertial visual support, function allowing at the same time structuring, location and follow-on of focalization, a visual comfort device according to the invention provides, via the monocular, lateral but sagittal route, an information system characterized by visual stimulations that are simplified as far as possible, and thus more easily accessible to straightforward perception.

In fact, a visual comfort device according to the invention is characterized in particular by the extreme simplicity of the visual message that it offers, more particularly due to its arrangement and its layout. Owing to the advantageous arrangement and composition of such a visual comfort device, the latter thus allows clear and concise visual information to be made available, and consequently simpler and quicker perception of said information by the brain of a human or animal user; therefore simpler and quicker analysis by the brain of a human or animal user, i.e. a better perceptive integration and better efficacy.

A visual comfort device according to the invention can be arranged such that it produces and displays an item of inertial information, in the form of an inertial matrix, given via a maximum of sixteen points or line intersections, per side or eye, or else by a maximum of three lines of variable lengths, per side or eye. Preferably, in order to provide only the necessary information to each eye, such inertial information can be arranged to be provided in the form of nine points. Such images, thus summarized, then allow quicker perception of the inertial information provided in the visual field.

According to a preferred but non-limitative example of a visual comfort device according to the invention, the latter can contain one or more lateral, sagittal screens; i.e. oriented front-to-rear or rear-to-front, attached very laterally, arranged so as to be used jointly or successively by each eye and positioned in the outer monocular visual field of each eye, like blinkers for horses, in order to provide visual information to one or both eyes, displayed in the form of points or lines, in a reduced, summarized manner. Said screens can thus cover a part of the monocular visual field of each eye. Optionally, in a variant or complementarily, in order to improve the vigilance and the perception of the outside world of a user, whether the latter is, non-limitatively, a pilot, a driver and/or any other on-board operator, of a visual comfort device according to the invention, the screen or screens of the latter can advantageously be translucent, or even transparent.

Preferably, but non-limitatively, in order to hold said screens in a determined optimal position, i.e. in the outer monocular visual field of each eye, a visual comfort device according to the invention can comprise a support cooperating in a fixed manner, using any suitable mechanical link, such as for example an anchoring, pivot, ball joint or else sliding link, with the screen or screens, and arranged so as to hold said screens in a determined position, such as mentioned above. Optionally, in order to facilitate the manufacture of a visual comfort device according to the invention, the support of the latter can comprise, advantageously but non-limitatively, a headband, a cap, a hat, a helmet, a mask or else a structure similar or identical to the general shape of a glasses frame, with or without eyepiece(s).

FIG. 1 shows an example of a visual comfort device in the form of a pair of glasses 10 according to the invention that contains two eyepieces 11 connected to two sidearms 12 intended to cooperate with the ears of a user in order to hold the pair of glasses in a position where the eyepieces 11 are located placed in the central visual field of the user. Two screens 13 are placed on the sidearms 12 of the glasses so that the screens are placed in the peripheral visual field of the user of said pair of glasses 10.

Figure 2:
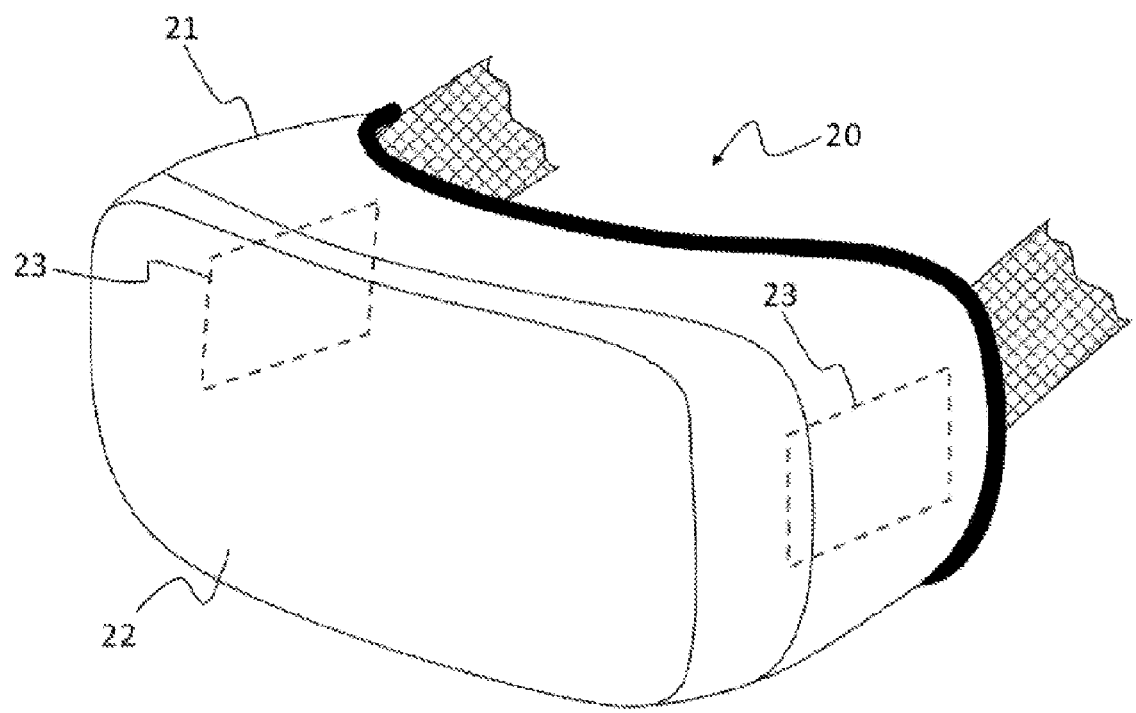
FIG. 2 represents a second embodiment of the invention in the form of a virtual reality mask.

FIG. 2 shows an example of a visual comfort device in the form of a virtual reality mask 20 comprising a housing 21 intended to be placed in the visual field of a user and containing at least one main screen 22 placed in the central visual field of a user. Two screens 23 are placed laterally inside the housing 21 such that they are placed in the peripheral visual field of the right eye and the left eye of the user, respectively.

According to different embodiments, the invention provides for the aforementioned screens 13 and 23 of a visual comfort device 10 or 20 according to the invention to be capable of cooperating in a fixed manner, using any suitable mechanical link, such as for example an anchoring, pivot, ball joint or else sliding link, with the screen or screens, and arranged so as to hold said screens 13 and 23 in a determined position relative to the types of support, such as a mask 20, a pair of glasses 10 or a mixed or augmented virtual reality simulator, or even be directly integrated with said support.

In a variant, according to the context of application or as a function of the needs, in particular as regards confined spaces created by a fixed or mobile support, such as for example cabins of aircraft or more generally vehicles, or even, optionally distanced a little further from the head, such screens can cooperate in a fixed manner with a support, according to any suitable mechanical link, such as for example an anchoring, pivot, ball joint or else sliding link, and arranged so as to hold said screens in a determined position, with all or part of the support so as to be held in a determined position. By way of non-limitative example, when a visual comfort device according to the invention is used in association with the cabin of a cockpit or more generally of a vehicle, said screens can then be held from the ceiling or else cooperate with the seat of a user, for example the headrest of a passenger or driver or more generally of a user of said device, or else a car seat for a child, when the user of said device is a child. To this end, a visual comfort device according to the invention can be arranged like blinkers cooperating with the seat, for example the headrest, of a passenger. Also, as a variant or complementarily, in order to be adapted according to the passenger or more generally the user, whether or not the latter requires permanent or temporary use of said visual comfort device, the invention provides for such a device, more particularly the screens, to be collapsible, retractable, or removable, by any means.

Figure 3:
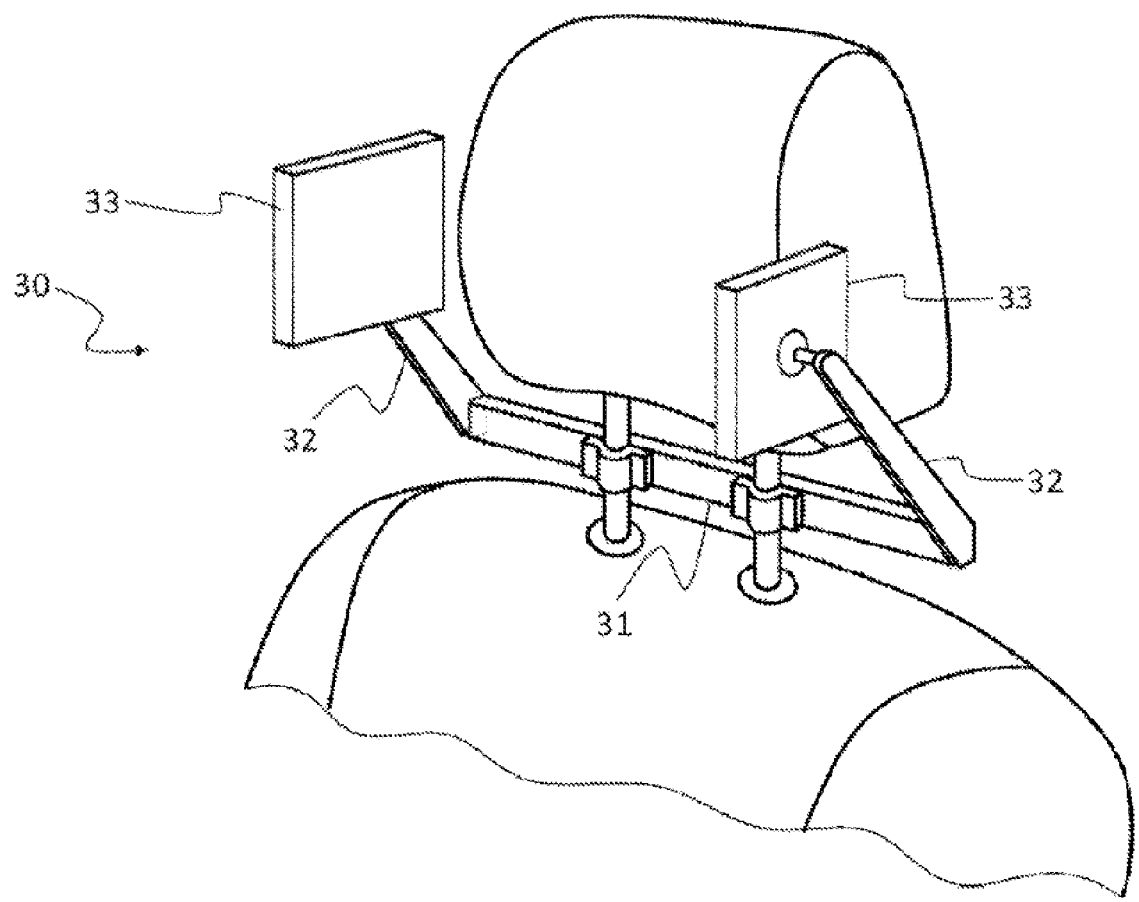
FIG. 3 represents a third embodiment of the invention intended to be fastened to a vehicle seat.

FIG. 3 shows an example of a visual comfort device 30 for a vehicle seat. The device 30 contains a fastening means 31 making it possible to render the device 30 firmly fixed to a vehicle seat and two linking arms 32 respectively connecting two screens 23 to the fastening means 31. The fastening means 31 is for example constituted by a bar equipped with two clamp connections cooperating with the mounting posts of a headrest. The linking arms can be mobile arms with respect to the fastening means 31 and to the screens 33 such that the screens can be adjusted in order to be placed at the level of one side of the head of a user of the seat in the peripheral visual field of said user. By way of non-limitative example, the link between the fastening means 31 and each of the linking arms 32 can be a pivot joint while the link between an arm 32 and a screen 33 can be a ball joint.

A visual comfort device according to the invention can contain a set of one or two screens attached to the outer side of the eyepieces of said mask, said glasses or said simulator, distributing all or part of the items of information, as the essential minimum, capable of being quickly perceived by the human brain; and optionally electronic elements, such as for example one or more inertial and/or magnetic sensor(s), an optional power source, and a processing unit, such elements cooperating together by coupling.

Figure 4:
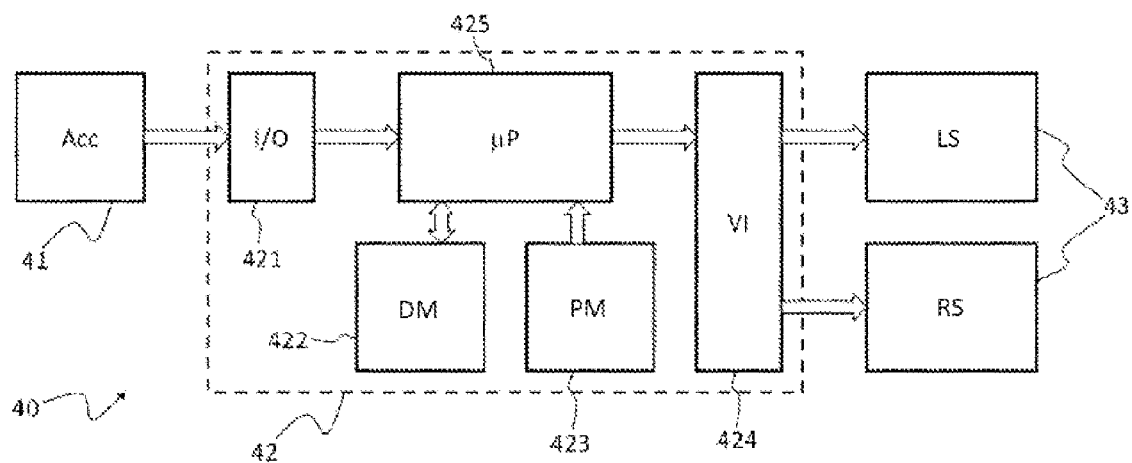
FIG. 4 represents a functional diagram of the invention.

FIG. 4 details a functional diagram of a visual comfort device 40 such that it can be implemented in the aforementioned pair of glasses 10, mask 20 or device 30.

The device 40 mainly contains an inertial sensor 41 connected to a processing unit 42, itself connected to two screens 43.

The inertial sensor 41 serves to measure an item of inertial information undergone by the visual comfort device 40. This inertial information can correspond to the inertial information experienced by the user when the visual comfort device is fixed to the user, such as for example a pair of glasses or a mask, or correspond to an item of inertial information from the environment of the user when the device is fixed to the environment of the user. The inertial sensor 41 can be of different types such as for example an inertial reference system, a gyroscope, one or more accelerometers, or else a detector of the Earth's magnetic field or a combination of these different types of sensors. What is important is that the inertial sensor 41 is able to supply an item of information representative of a movement undergone and/or an acceleration undergone by the device in order to be capable of preparing an inertial matrix representative of this movement.

The processing unit 42 contains an input/output interface 421, a data memory 422, a program memory 423 and a video interface 424, all connected to a microprocessor 425. According to a preferred embodiment, the processing unit 42 is a circuit of the microcontroller type, which integrates the circuits 421 to 425 or equivalent circuits for carrying out the same function. The input/output interface 421 is connected to the inertial sensor 41 by a wired or wireless connection of a known type in order to receive sampled inertial data from the inertial sensor 41 and to supply them to the microprocessor. The data memory 422 is a working memory, for example of the RAM type, which makes it possible to store all the data used and calculated by the microprocessor 425. The program memory 423 is a non-volatile memory that stores the programs implemented by the microprocessor 425 as well as configuration data that make it possible to initialize the data memory during activation of the visual comfort device. The video interface 424 receives data from the microprocessor 425 that correspond to images to be displayed on the screens 43. The video interface 424 shapes control and image signals in order to supply them to said screens 43.

The screens 43 can have a very small dimension, for example of the order of an inch diagonally, if it is desired to integrate them in a pair of glasses, or a slightly larger dimension, for example of the order of five inches diagonally, if it is desired to fasten them to a headrest. A resolution of 320×200 pixels is sufficient to display a reference inertial matrix. However, a lower resolution can be used if the matrix has only points, and a higher resolution can be used to have a greater fluidity of movement for a matrix containing line intersections.

Among the programs contained in the program memory 423, a program that comprises a plurality of instructions, the execution of which by the microprocessor 425 implements a method for converting the inertial information supplied by the inertial sensor 41 to at least one image to be displayed on a screen 43.

According to a first embodiment, the method implemented by the microprocessor 425 initializes in the data memory 422 an inertial matrix to be displayed on the screen. Then, on receiving an item of inertial information, the microprocessor 425 calculates a displacement of the inertial matrix on the screen 43 corresponding to the reverse movement to that indicated by the item of inertial information.

Figure 5:
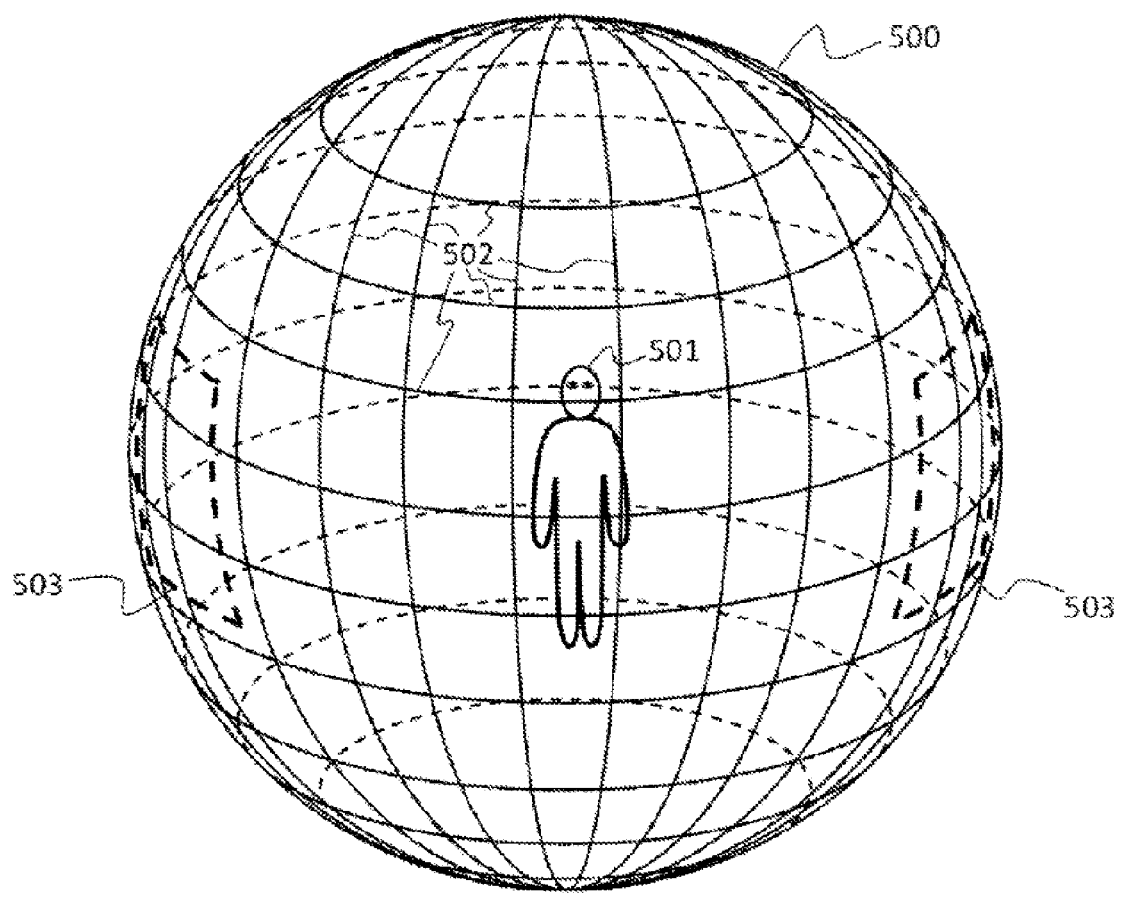
FIGS. 5 to 7 illustrate a first preferred embodiment of an inertial matrix according to the invention.
Figure 6:
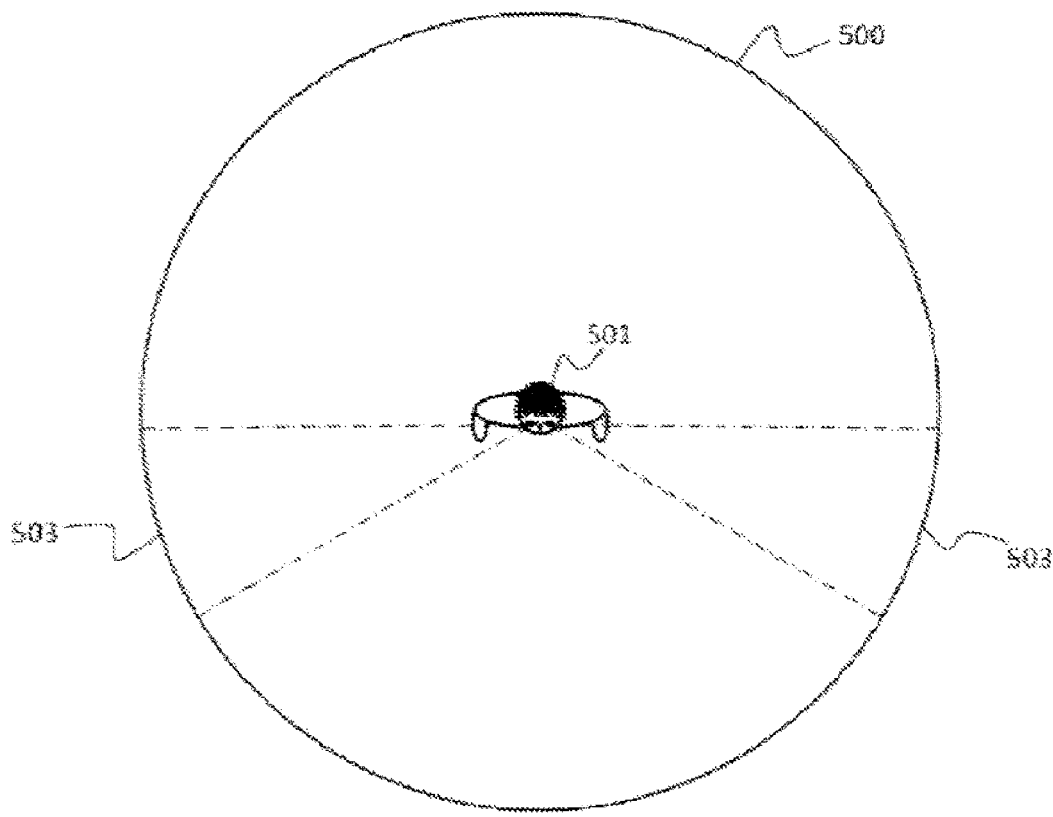
Figure 7:
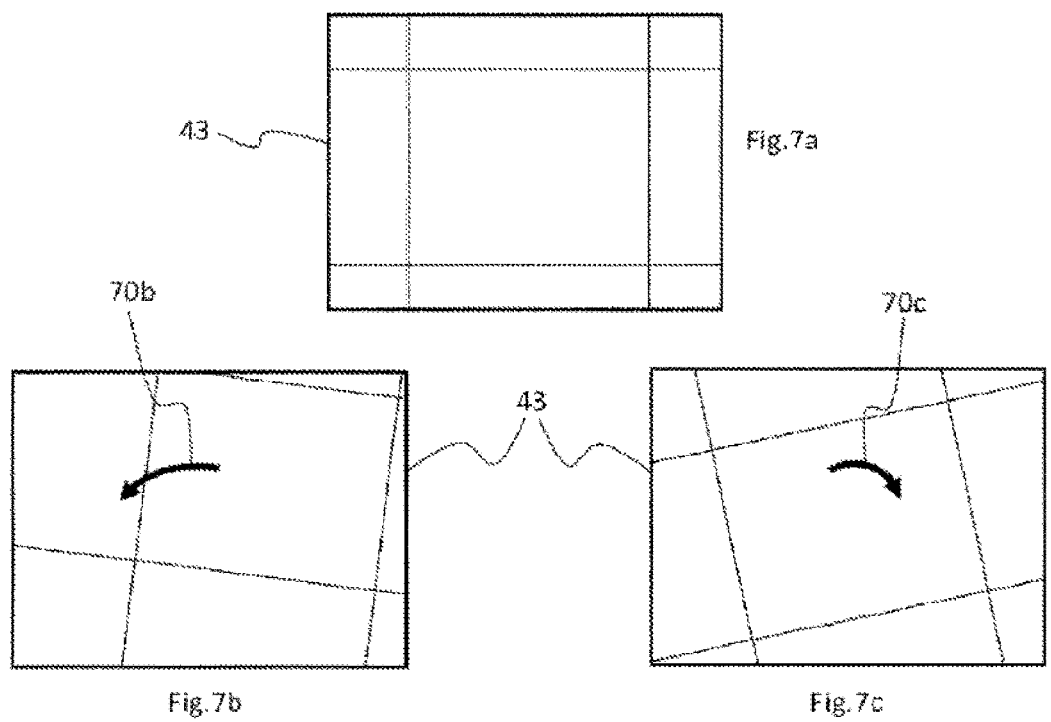

FIGS. 5 to 7 illustrate a second embodiment in which the visual comfort device 40 is firmly fixed to the user, such as for example in the case of the pair of glasses 10 or the virtual reality mask 20. The method implemented by the microprocessor 425 can consist of the creation of a virtual constellation or matrix 500 around the user 501, said virtual matrix 500 having a fixed position in the space surrounding the user 501. In the example in FIG. 5, the virtual matrix 500 corresponds to a sphere containing a plurality of line intersections 502, in such a way as to supply an inertial matrix formed of line intersections to the user 501. The microprocessor 425 then determines a position of the user 501 inside the virtual constellation 500 as a function of the inertial information. When the position of the user 501 has been determined, windows 503 can be positioned on the virtual matrix 500 to correspond to the peripheral visual field of the user 501 in which the screens 43 are placed, as shown in FIG. 6. The microprocessor 425 then extracts the images corresponding to the windows 503 from the virtual matrix 500 in order to supply them to the video interface 424 so as to display them on the screens 43.

FIG. 7 illustrates the images displayed on a screen 43 as a function of inertial information. FIG. 7a shows an inertial matrix corresponding for example to an initialization position. The initialization position can correspond to the positioning of the matrix with respect to the user when the visual comfort device 40 is powered up, or when a press-button (not shown) present on the device is pressed in order to allow its initialization. The microprocessor 425 then stores the item of inertial information supplied by the inertial sensor 41 as being the fixed position of the virtual matrix 500. The image thus obtained corresponds to a position of the user 501 who is placed as shown in FIG. 5.

After initialization of the device, the inertial information is compared to the inertial information of initialization to indicate a displacement of the user 501 with respect to said initialization position, such as for example illustrated by the arrows 70b and 70c respectively in FIGS. 7b and 7c. The microprocessor 425 calculates the position of the user 501 with respect to the virtual matrix as a function of the displacement thus determined. Images corresponding to the displacement can then be extracted and displayed on the screen 43 as shown respectively in FIGS. 7b and 7c.

This embodiment can be adapted to other different types of inertial matrix. FIGS. 8 and 9 illustrate a similar method for obtaining an inertial matrix constituted by points. The virtual matrix 500 in FIG. 8 is constituted by a multitude of points 802. The positioning of the windows 503 is carried out in the same manner as described above in connection with FIGS. 5 to 7. The microprocessor 425 can then extract and display on the screens 43 the representative images of the inertial matrix that are shown in FIG. 9. FIG. 9a corresponds to the initialization position and FIGS. 9b and 9c correspond to the images of the inertial matrix affected by a movement represented by the arrows 90b and 90c.

Figure 10:
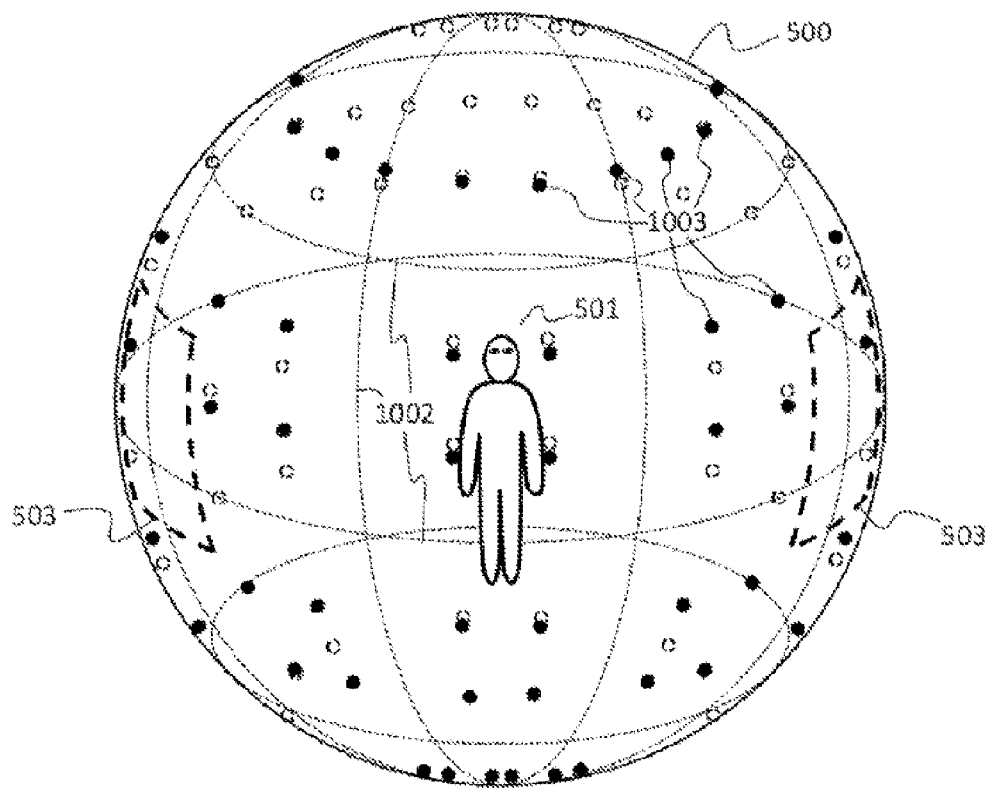
FIGS. 10 and 11 illustrate a third preferred embodiment of an inertial matrix according to the invention.
Figure 11:
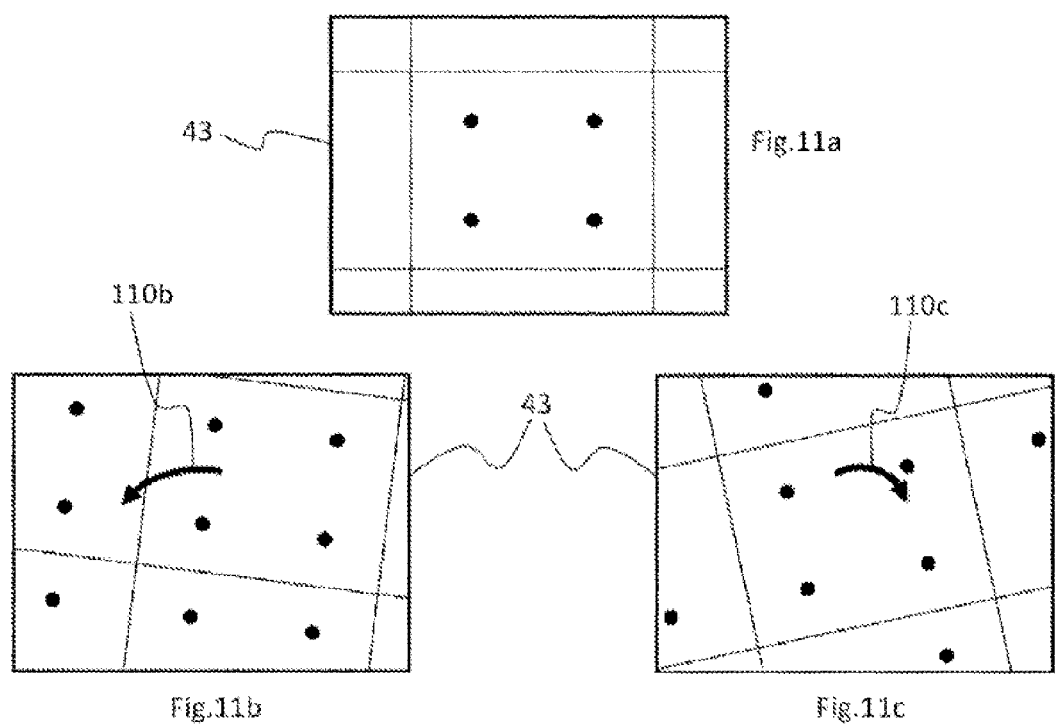

According to a variant, FIGS. 10 and 11 illustrate a similar method for obtaining an inertial matrix constituted by a mixture of line intersections and points. The virtual matrix 500 in FIG. 10 is constituted by a plurality of lines 1002 and a multitude of points 1003. The positioning of the windows 503 is carried out in the same manner as described above in connection with FIGS. 5 to 7. The microprocessor 425 can then extract and display on the screens 43 the representative images of the inertial matrix that are shown in FIG. 11. FIG. 11a corresponds to the initialization position and FIGS. 11b and 11c correspond to the images of the inertial matrix affected by a movement represented by the arrows 110b and 110c.

Any other form of inertial matrix remains possible, provided the number of points and/or line intersections displayed on a screen remains limited so as not to supply too much information in the peripheral visual field of a user.

The examples of implementation detailed with the aid of FIGS. 5 to 11 refer to a visual comfort device firmly fixed to the user. Thus, any movement of the device corresponds to a movement of the user. The movement of the inertial matrix displayed on the screens 43, for its part, corresponds to a movement experienced by the user. Alternatively, when the visual comfort device 40 is not firmly fixed to the user, for example when it is fixed to a seat, the inertial matrix display must correspond to a movement experienced by the seat. In fact, the movement experienced by the seat is the same as the movement experienced by the user if the user is immobile with respect to the seat. When the user moves with respect to the seat, the inertial matrix displayed is representative of the movement of the seat and constitutes a visual reference that is added to the movement of the user with respect to the seat. What is important is for the image of the inertial matrix to be representative of the movement experienced by the screen 13, 23, 33 or 43, which displays it such that the user's perception corresponds with the movement experienced by their inner ear.

The visual comfort device 40 has been described with two screens. However, a single screen can be sufficient, as it is possible to integrate the inertial sensor 41 and the processing unit 42 in the housing of a screen 43. In this way, a device using two screens can contain two devices 40, independent of one another but carrying out the same type of processing.

The processing unit 42 can also be replaced by any other processing unit, providing the latter is capable of converting an item of inertial measurement information to an inertial matrix image.

The invention claimed is:

1. Visual comfort device comprising:
    at least one inertial sensor configured to obtain inertial information,
    at least one screen, the screen for positioning laterally in an outer monocular field of an eye of a user, and
    a processing unit coupled to the inertial sensor and to the screen, wherein
    the processing unit is configured to:
    upon initialization of the device, produce a virtual matrix having a position in space surrounding the user,
    compare the inertial information upon initialization of the device to current inertial information to determine a displacement of the virtual matrix relative to its previous position, in a reverse movement to that indicated by said current inertial information, and
    extract a portion of the virtual matrix to display on the screen an inertial matrix representative of an image of the extracted portion of the virtual matrix, said displayed inertial matrix containing a maximum of sixteen points and/or line intersections.

2. Device according to claim 1, containing two screens arranged to be placed in the outer monocular field of each eye of a user, each screen displaying an inertial matrix.

3. Device according to claim 2, in which the inertial matrix displayed on a screen contains at most nine points and/or line intersections.

4. Device according to claim 1, in which the inertial sensor is fixed to the screen and supplies the inertial information to the processing unit; the inertial information being representative of an inertial orientation of said screen.

5. Device according to claim 1, in which the inertial sensor comprises one or more of the types of sensors selected from the following list:
one or more accelerometers,
gyroscope,
inertial reference system,
magnetic field detector.

6. Device according to claim 1, also containing a fastener for a vehicle seat and at least one linking arm linking the at least one screen to the fastener such that the screen is placed at the level of one side of the head of a user of the seat, so that the screen is placed in the peripheral visual field of said user.

7. Pair of glasses comprising two sidearms for engaging the ears of a user, and containing at least one device according to claim 1, at least one screen being fastened on one of the sidearms such that the screen is placed laterally in the peripheral visual field of the user.

8. Virtual reality mask comprising a housing to be placed in the visual field of a user and containing at least one main screen placed in the central visual field of a user, and containing a device according to claim 2 and in which the two screens are placed laterally inside the housing such that they are placed in the peripheral visual field of a right eye and a left eye of the user, respectively.

* * * * *